US00PP10634P

United States Patent [19]

Hureau

[11] Patent Number: Plant 10,634

[45] Date of Patent: Oct. 6, 1998

[54] STRAWBERRY PLANT NAMED 'DARSANGA'

[75] Inventor: Robert Hureau, Noisy sur Ecole, France

[73] Assignee: Societe Civile Darbonne, France

[21] Appl. No.: 710,712

[22] Filed: Sep. 18, 1996

[51] Int. Cl.[6] ..... A01H 5/00

[52] U.S. Cl. ..... Plt./48

[58] Field of Search ..... Plt./48, 49

[56] References Cited

PUBLICATIONS

UPOVROM citation for 'Darsanga' FR NLI 132091, Mar. 10, 1989.

UPOVROM citation for 'Darsanga' FR PBR 132091, Apr. 10, 1990.

*Primary Examiner*—James R. Feyrer

*Attorney, Agent, or Firm*—Christie, Parker & Hale, LLP

[57] ABSTRACT

A strawberry plant producing conical fruit of dark red internal and external color.

4 Drawing Sheets

BACKGROUND OF THE INVENTION

This disclosure involves a newly developed strawberry, Fragaria Xannanassa Duch. plant, which has been denominated 'Darsanga' for purposes of international recognition. The new variety of strawberry was created in a breeding program by crossing as female parent the variety known as 'Tufts' and as male parent the variety known as 'Korona'. The varietal denomination of the new variety is 'Darsanga'. The plant of this invention is the resulting selection, from the stated cross, which was based on a novel and superior combination of characteristics which will be disclosed infra, as well as depicted in the drawing. The combination of characteristics reflects the novelty of this plant and of its potentially advantageous use in the production of commercial strawberry fruit as well as in planned breeding programs for the development of further superior varieties.

'Darsanga' was grown and asexually propagated by runners and tissue culture in Thiais, France. Asexual propagation and testing has demonstrated that the combination of traits of the new variety are fixed and retained true to type through successive generations.

SUMMARY OF THE INVENTION

Among the characteristics which distinguish the new variety from other varieties of which I am aware are a combination of traits that include production of conical, fruit of dark red internal and external color. The plant of this application is further characterized as distinct by the apparent uniformity of the size and shape of the fruit, the short ripening period of the fruit, the fruit, the lack of locules in the fruit, the calyx characteristics, the apparent positioning of the fruit above the growing surface by strong peduncles, and the apparent firmness of the fruit. There is no known similar variety for comparison.

BRIEF DESCRIPTION OF ILLUSTRATIONS

The accompanying photographs show typical specimens of the new variety, including fruit, foliage and flower, in color as nearly true as it is reasonably possible to make in color illustrations of this character.

DESCRIPTION OF THE NEW VARIETY

Figure 1:
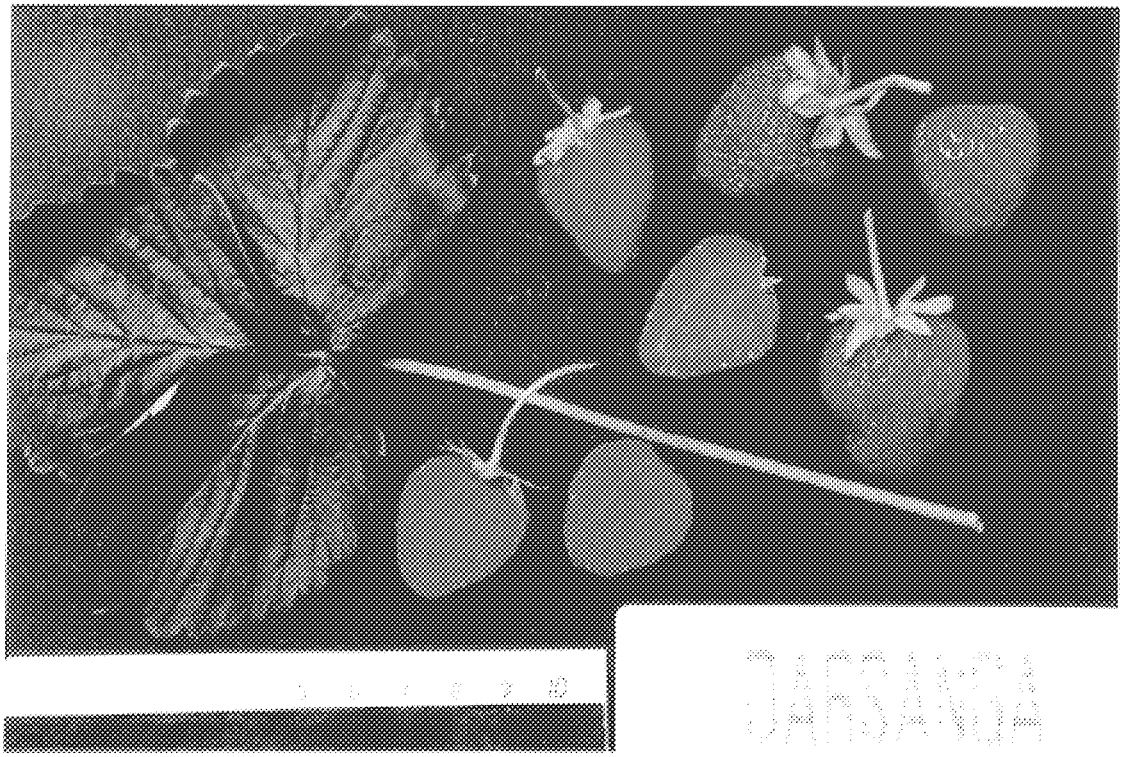
FIG. 1 shows typical fruit in cross section, llustrating the flesh and flesh coloration and external color, and a leaf.
Figure 2:
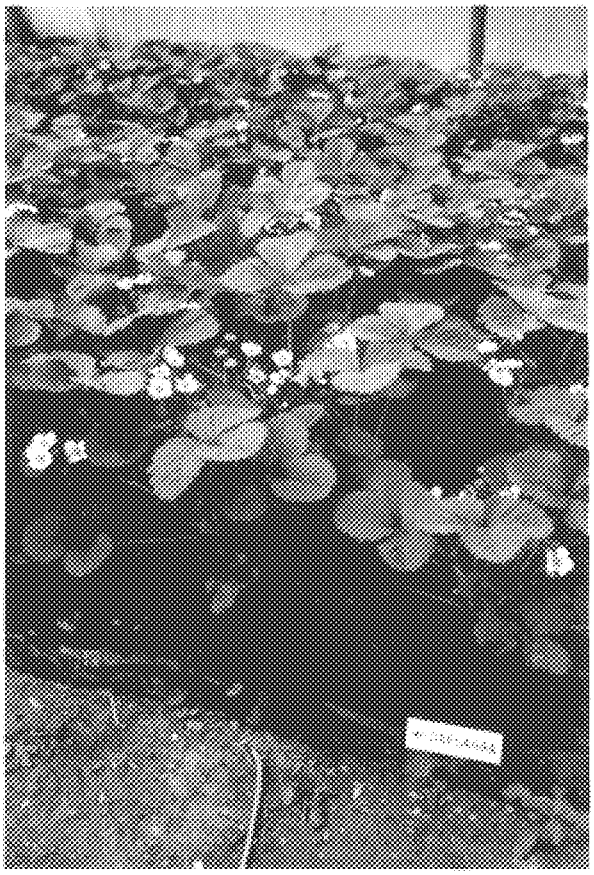
FIG. 2 shows plants of the new variety.
Figure 3:
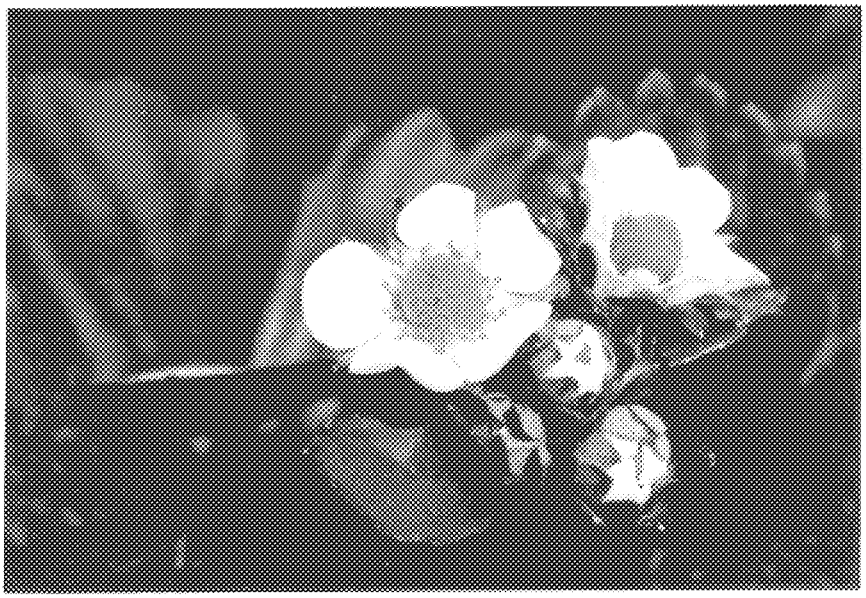
FIG. 3 shows flowers and buds.
Figure 4:
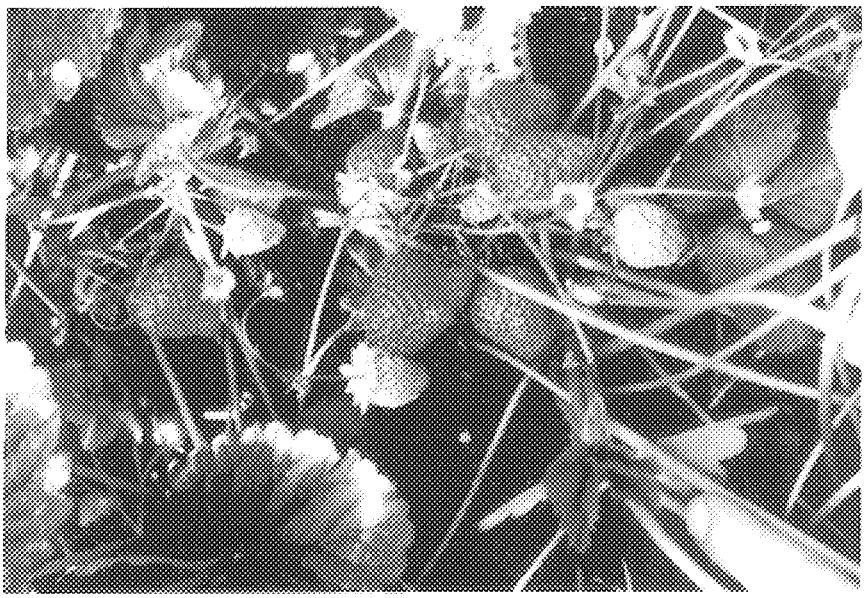
FIG. 4 shows fruit growing on a plant.

The following detailed description of the new variety is based upon observations taken of plants and fruit grown outdoors in Thiais, France, during the month of June.

The following description is in accordance with UPOV terminology and the color terminology herein is in accordance with The Royal Horticultural Society Colour Chart (R.H.S.C.C.). The color and phenotypic expression may vary depending upon environmental, seasonal, climatic and cultural conditions.

Propagation

The new variety may be propagated by runners and micropropagation, although other known methods of propagating strawberry plants may be used. A characteristic of the new variety is that it is very strong in "running" and easy to propagate. It is well adapted to cultivation in matted rows.

General

'Darsanga' is a short day variety with upright growth habit and abundant runner production. Semi-erect fruit peduncles and synchronism of ripening make the new variety suitable for mechanical harvesting.

Plants

Size and shape: Globose habit with a medium density compared to Senga Sengana which is globose flat habit and high density.

*Height.*—20–30 cm.

*Width.*—25–30 cm.

Crown: No branch compared to Senga Sengana which give plants with several crowns.

Planting time: May for cold store plants at Gisors (France).

Growing preferences: Continental climate.

Chilling requirement: 700–900 H at less than 6°–7° C. (Senga Sengana need more chilling).

Leaves:

*Size.*—Large, approximately for mature leaves 20 cm long and 8–10 cm wide with weak blistering.

*Leaf color.*—Upper side: dark green, near 135A, 135B, but lighter color than Senga Sengana leaves. Underside: 191B.

Leaflet:

*Number.*—3 leaflets as long as broad.

*Texture.*—Medium thickness.

*Serration.*—Base and edge's shape slightly rounded.

Petioles:

*Size.*—Short, approximately 110–130 mm with a diameter of 2 mm.

*Position of hairs.*—Outward.

*Coloration.*—Light green.

*Stipules.*—Green coloration.

Runners: Very numerous, vigorous with a grey red color, thin (1 mm of diameter).

*Pubescence.*—Hairs upwards.

Inflorescence:

*Size.*—Medium.

*Peduncles.*—Medium size and oblique hair implantation.

*Fruiting truss.*—Semi-erect, long approximately 200 mm, strong with a diameter of 3–4 mm. Senga Sengana fruiting truss are more prostate, short.

Flowers:

*Abundance of flowers.*—Very numerous.

*Bud color.*—White.

*Size.*—Medium.

*Sepals.*—Numerous, shorter than bud, near 135C.

*Calyx.*—Size: Smaller than corolla and inner calyx of same size than outer calyx. Sepals: Light green coloration.

*Petals.*—Five or more on flowers, as long as broad, overlapping petals.

*Position relative to foliage.*—Above or same level.

*Time of flowering.*—Middle of May (50%).

Reproduction organs:

*Anthers.*—Near 19A.

*Pollen.*—Near 19A.

*Stigma.*—Near 19A to 19B.

Fruit:

*Size and shape.*—Primary fruit: medium, conical, weighing 9–12 g, production starts in the second week of June. Senga Sengana fruits are more round. Secondary fruit: smaller 5–9 g, similar in shape to primary fruits.

*Seed characteristics*—Numerous achenes inserted below surface with yellow color.

*Insertion of calyx.*—Position of calyx: Detached. Size of calyx in relation to fruit diameter: Smaller. Calyx removal: Difficult, Senga Sengana fruits are easier to decap.

*Color-exterior and flesh.*—Even internal and external color dark red, near 46A external, near 45A internal.

*External surface* (*skin*).—Color: Dark red, 46A, same as Senga Sengana. Glossiness: Medium, stronger than Senga Sengana. Shape: Conical fruit, longer than Senga Sengana. Firmness: Very firm (60–70 g.force with a penetrometer on a scale from 0 to 100), more resistant to bruises than Senga Sengana (40–50 g.force).

*Flesh.*—Color: Dark red, near 45A, uniform without white strain unlike Senga Sengana. Firmness: Very firm (200–250 g.force with a penetrometer on a scale from 0 to 500 g.force), firmer than Senga Sengana (100–160 g.force) Texture: Homogeneous, full core, not very juicy. Senga Sengana appears more juicy with a woolly core.

*Taste.*—Medium sweetness (brix=7–10) and low acidity (68–70 meq H+) as Senga Sengan.

*Aroma.*—Fresh, green, light fruited with little astringency. Absence of the "cheese" note observed in Senga Sengana.

*Shell life.*—Very good quality, remains glossy and firm after two days at 20° C. without rotting compared to Senga Sengana which rots easily and become darker during storage.

*Time of ripening.*—Mid June (50% red fruit).

*Fruit bearing habit.*—Not remontant.

*Thawing ability.*—The juice lost during thawing of frozen fruit is half the amount observed with Senga Sengana.

*Processing ability.*—Maintains good integrity of fruit upon processing. Senga Sengana is much less resistant to the processing.

*Disease resistance.*—Good general tolerances to pathogens observed in the field.

What is claimed is:

1. A new and distinct variety of strawberry plant, substantially as shown and described.

* * * * *